United States Patent
Van Dyk et al.

(10) Patent No.: US 6,904,125 B2
(45) Date of Patent: Jun. 7, 2005

(54) PHANTOM FOR EVALUATING NONDOSIMETRIC FUNCTIONS IN A MULTI-LEAF COLLIMATED RADIATION TREATMENT PLANNING SYSTEM

(75) Inventors: Jake Van Dyk, London (CA); Andrea Leigh McNiven, London (CA)

(73) Assignee: Cancer Care Ontario, Toronto (CA)

( * ) Notice: Subject to any disclaimer, the term of this patent is extended or adjusted under 35 U.S.C. 154(b) by 135 days.

(21) Appl. No.: 10/618,910

(22) Filed: Jul. 14, 2003

(65) Prior Publication Data

US 2005/0013406 A1 Jan. 20, 2005

(51) Int. Cl.⁷ .................................................. A61N 5/10
(52) U.S. Cl. ........................................ 378/65; 378/207
(58) Field of Search .................................. 378/65, 207

(56) References Cited

U.S. PATENT DOCUMENTS

| | | | |
|---|---|---|---|
| 4,672,212 A | 6/1987 | Brahme | |
| 4,987,309 A | 1/1991 | Klasen et al. | |
| 5,438,991 A | 8/1995 | Yu et al. | |
| 5,818,902 A | 10/1998 | Yu | |
| 6,052,430 A | 4/2000 | Siochi et al. | |
| 6,052,436 A | 4/2000 | Huttner et al. | |
| 6,260,999 B1 | 7/2001 | Wofford et al. | |
| 6,330,300 B1 | 12/2001 | Siochi | |
| 6,349,129 B1 | 2/2002 | Siochi | |
| 6,449,335 B1 | 9/2002 | Siochi | |
| 6,459,769 B1 | 10/2002 | Cosman | |
| 6,577,707 B2 | 6/2003 | Siochi | |

OTHER PUBLICATIONS

Ayyanger, K., et al., Experimental Verification of a Three–Dimensional Dose Calculation Algorithm Using A Specially Designed Heterogeneous Phantom, Med. Phys. 20, 1993, pp. 325–329.

AAPM Radiation Therapy Committee Task Group 53: Quality Assurance for Clinical Radiotherapy Treatment Planning, Benedict Frass et al.; Med. Phys. 25(10), Oct. 1998, pp. 1773–1829.

Craig et al., A Quality Assurance Phantom for Three–Dimensional Radiation Treatment Planning, Int. J. Radiation Oncology Biol. Phys., vol. 44, No. 4, pp. 955–966, 1999.

*Primary Examiner*—Craig E. Church
(74) *Attorney, Agent, or Firm*—Philip M. Weiss; Weiss & Weiss

(57) ABSTRACT

A phantom for evaluating nondosimetric functions in radiation therapy installation having a patient couch and a gantry with a head thereon for generating a multi-leaf collimated beam, wherein the beam is directed toward the couch at an orientation dictated by relative orientations of the couch and gantry. The phantom comprises a base adapted for disposition on the couch, and a component mounted to the base for rotation in accordance with the relative orientations of the couch and gantry. The component incorporates a plurality of known geometrical structures corresponding in shape to the multi-leaf collimated beam. Upon imaging the component, nondosimetric functions may be evaluated by comparing the known geometrical structures with images of the structures and identifying discrepancies therebetween.

15 Claims, 19 Drawing Sheets

PHANTOM FOR EVALUATING NONDOSIMETRIC FUNCTIONS IN A MULTI-LEAF COLLIMATED RADIATION TREATMENT PLANNING SYSTEM

FIELD OF THE INVENTION

The present invention is directed in general to quality assurance of radiation therapy installations and more specifically to a phantom for testing nondosimetric functions in radiation therapy installations that use a multi-leaf collimated beam.

BACKGROUND OF THE INVENTION

A radiation therapy installation typically includes such equipment as a CT scanner, CT simulator software, radiation treatment planning software, a linear accelerator, a multi leaf collimator, and a portal imager. Radiation treatment planning systems and image based simulators such as CT and MRI are known in the medical arts for treatment and diagnosis of disease. For example, a radiation therapy device typically includes a gantry, which can be rotated around a horizontal axis of rotation, and a patient couch, which can be rotated about a vertical axis. A linear accelerator is located within the gantry for generating a high energy radiation beam for therapy. During treatment, the beam is directed at a particular treatment zone of a patient, which is located at or about the intersection of the two axes of gantry rotation, otherwise known as the isocenter.

It is also known to use computer-controlled, motorized, mechanical shaping of radiation beams generated by such systems to produce conformal beam shaping. For example, multi-leaf collimators (MLCs) are available from Varian, Inc. of Palo Alto, Calif., Siemens Oncology Care Systems, Inc. of Concord, Calif., and others. Such multi-leaf collimators typically incorporate radiation shielding material such as tungsten leaves to conform the radiation beam more closely to a target volume, such as a tumor near vital organs in the patient's body, without exposing the surrounding organs to harmful radiation. As a result, the dosage of radiation can be increased when compared to that administered to the patient without the MLC. Examples of such systems are set forth in U.S. Pat. Nos. 4,672,212; 5,818,902; 6,577,707; 6,459,769, and others.

Quality assurance of dosimetric functions of radiation therapy planning systems and image based simulators is mandated to ensure accurate radiation planning for medical treatment. To that end, water-based phantoms are well known in the art (e.g. Ayyangar K., et al, Experimental Verification of a Three-Dimensional Dose Calculation Algorithm Using a Specially Designed Heterogeneous Phantom, *Med. Phys.* 20, 1993, pp. 325–329). More recently, increasing attention has been paid to quality assurance (QA) of the nondosimetric functions of such systems. For example, the AAPM Radiation Therapy Committee Task Group 53: Quality Assurance for Clinical Radiotherapy Treatment Planning, Benedick Fraass et al; *Med. Phys.* 25 (10), October 1998, pp. 1773–1829 highlights areas of nondosimetric QA of treatment planning that need to be addressed. The TG-53 report specifically addresses the need for QA of image acquisition, anatomical representation, beam display, plan evaluation tools, hard copy output, and other features.

Tim Craig, Dennis Brochu and Jake Van Dyk have disclosed a phantom for the QA of many nondosimetric features of three-dimensional radiation treatment planning systems and CT simulators (see A Quality Assurance Phantom for Three-Dimensional Radiation Therapy Treatment Planning, *Int. J. Radiation Oncology Biol. Phys.*, Vol. 44, No. 4, pp. 9555–966, 1999). The phantom of Craig et al. comprises a rotatable component to assess the display of the radiation beam graphics and CT set data manipulations, and a stationary component to assess the treatment of anatomical volumes and the conversion of CT numbers to relative electron density.

Although the system of Craig et al facilitates the implementation of a program consistent with the recommendations of TG-53, there is no provision for testing the integrity of treatment planning systems and CT simulators in the display of MLC-shaped fields on transverse or reconstructed images.

SUMMARY OF THE INVENTION

According to the present invention, a phantom is provided that reproduces the features of a collimated beam, in particular the edges of the beam, from the linear accelerator in a radiation therapy installation. More particularly, the multi-leaf collimator beam geometry phantom of the present invention provides a plurality of air-to-acrylic interfaces corresponding to square and pyramidal collimated beam apertures near the isocenter of a therapy device. The divergent surfaces align with the edges of the collimated beam from a conventional linear accelerator. The interfaces are easily seen on CT images. The phantom includes a metal wire for aligning the phantom with images of the scanner and a small metal ball for referencing the center of the phantom. The phantom includes laser alignment marks for aligning the phantom with the CT scanner and linear accelerator.

According to another aspect of the present invention, a method for calibrating a CT-scanner in a radiation treatment planning installation includes one or more of the steps of acquiring a CT data set via scanning of the phantom, registration of the treatment planning coordinate system with the phantom coordinate system, verifying image acquisition and transfer from the scanner to the treatment planning or simulator software, assessment of the display of radiation beam geometry in the software, assessing the accuracy of the anatomy displayed on multiplanar CT image reconstructions, and checking the geometric accuracy of digitally reconstructed radiograph (DRR) images. In addition to the QA of radiation treatment planning or simulator software, the multi-leaf collimator beam geometry phantom of the present invention may be used as part of a QA program for film or electronic portal imaging.

These together with other aspects and advantages, which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

A description of the preferred embodiment is set forth in detail below, with reference to the following drawings, in which.

DETAILED DESCRIPTION OF THE PREFERRED EMBODIMENT

Figure 1:
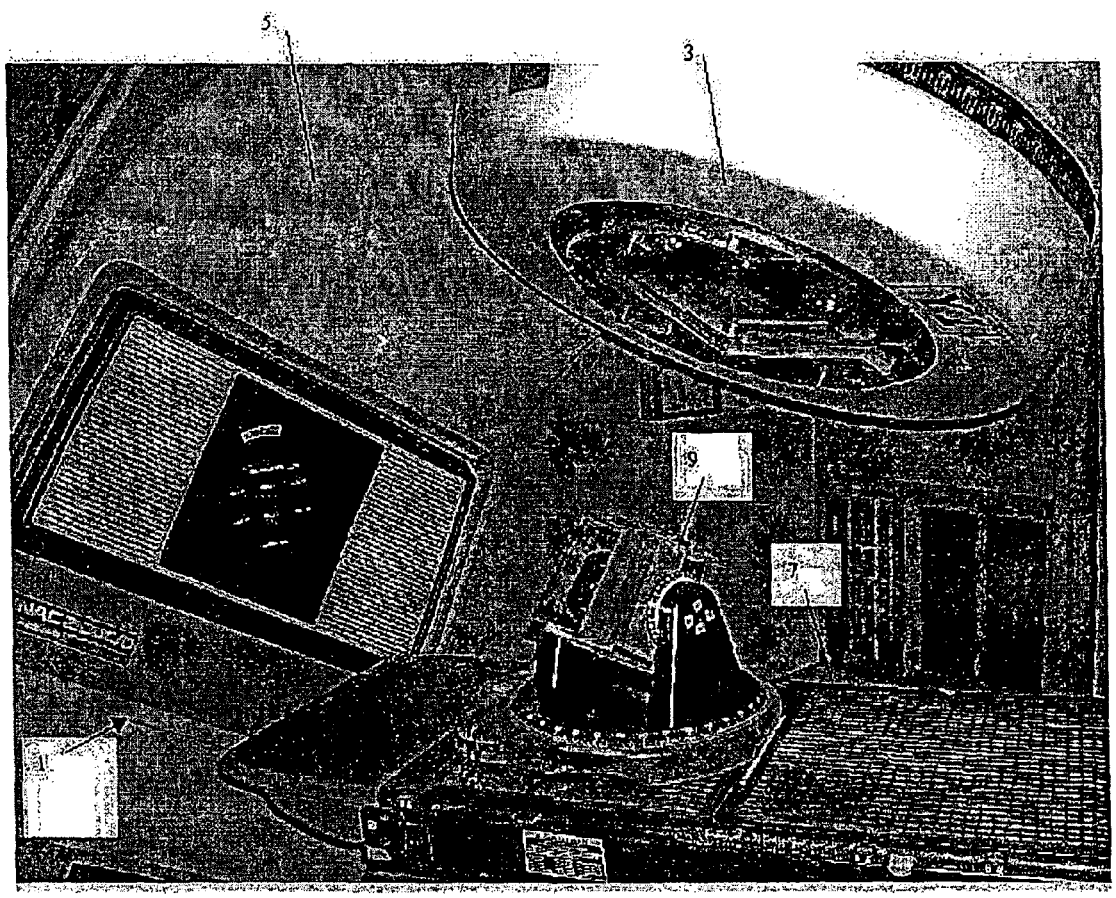
FIG. 1 shows the phantom of the present invention positioned on the patient couch of a radiation treatment device equipped with a multi-leaf collimator.

With reference to FIG. 1, radiation treatment device 1 incorporates a multi-leaf collimator (not shown) within the treatment head 3. The head 3 is fixed to a gantry 5 that swivels about a horizontal axis around a patient couch 7. A linear accelerator is located within the gantry 5 for generated high-energy radiation for therapeutic treatment. Suitable orientation of the beam is achieved relative to the patient by selecting appropriate gantry and couch angles of rotation. The phantom 9 of the present invention is shown positioned on the couch 7 for receiving radiation from a conventional radiation treatment device 1 (i.e. a linear accelerator with a 100 cm source axis distance (100 cm from source to isocenter 33)). Although the device 1 is shown as a linear accelerator in FIG. 1, the phantom of the present invention may be used to equal advantage to assess QA of an MRI.

Figure 2:
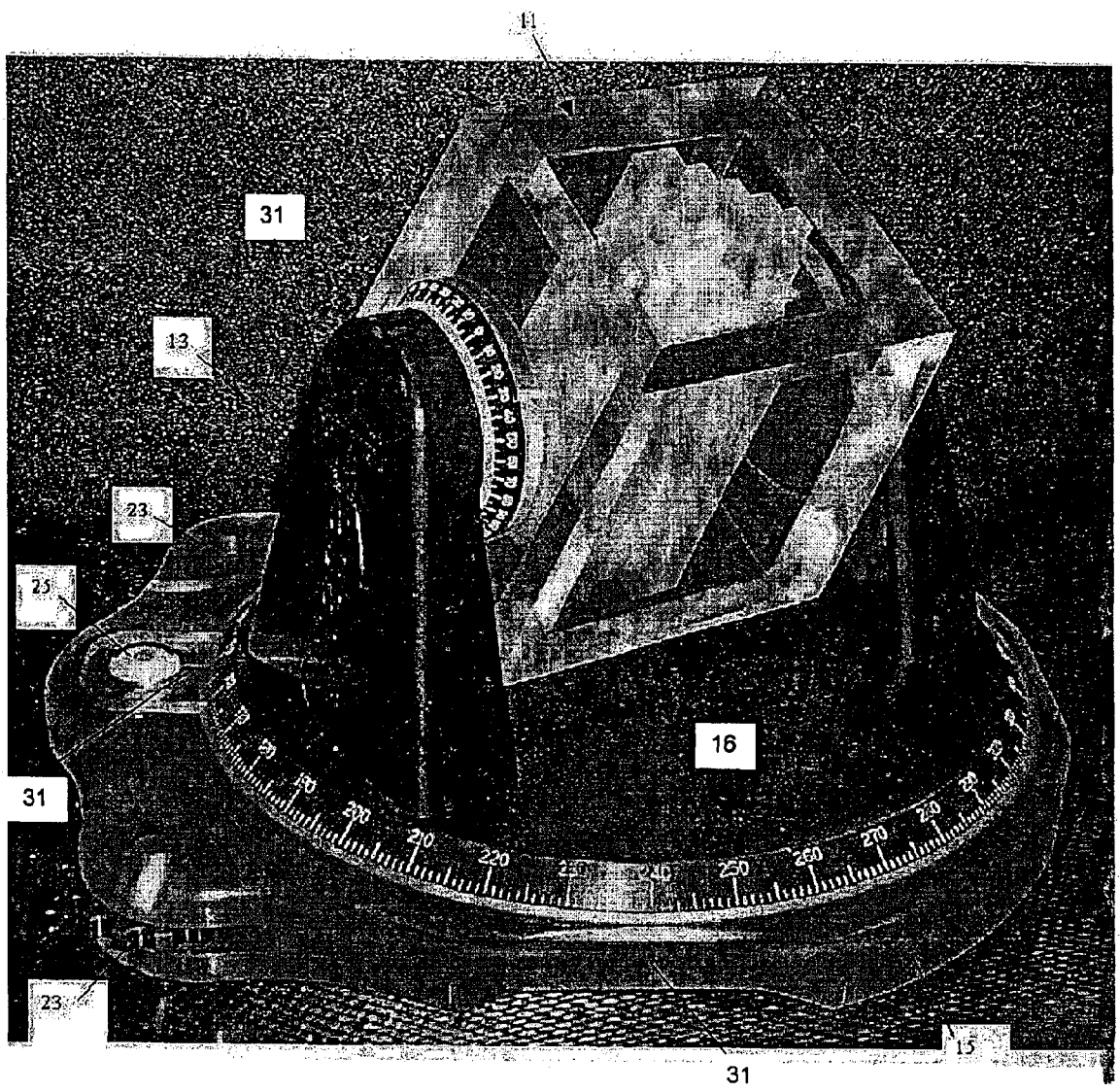
FIG. 2 is a perspective view of the phantom of the present invention.
Figure 3:
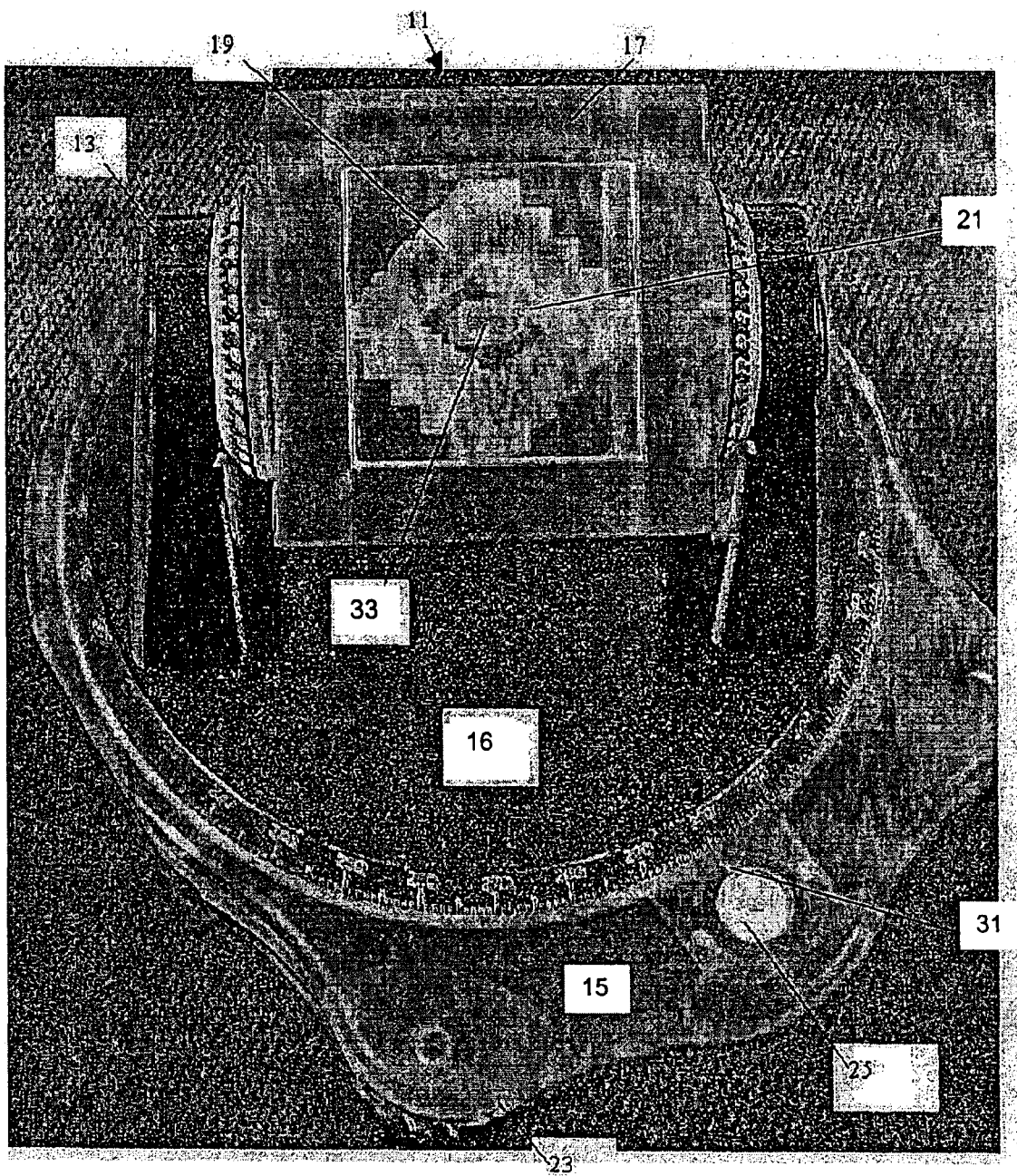
FIG. 3 is a plan view of the phantom of the present invention.

As shown in FIGS. 2 and 3, the phantom 9 includes a rotatable component 11 that is fixed in a yoke 13. Yoke 13 is fixed to a platter 16, which is in turn rotatably mounted to a base 15. The component 11 is free to rotate within yoke 13, and platter 13 is free to rotate on base 15, thereby providing two degrees of rotational freedom, corresponding to gantry 5 and couch 7 rotations. The beam display is assessed by creating a beam with isocenter 33 (see FIG. 6) at the center of the rotatable component 11, with gantry and couch rotations corresponding to the orientation of the component 11 when the phantom is scanned.

The rotational component 11 includes a tapered cubic outer portion 17 that, in transverse cross-section through the isocenter 33, is characterized by outer wall length and width of approximately 150 mm and inner wall length and width of approximately 100 mm (i.e. wall thickness of approximately 25 mm). A pyramid-shaped portion 19 is disposed within the portion 17. In transverse cross-section through the isocenter 33, the pyramid-shaped portion 19 is characterized by a step-shaped outer wall with rise and run of each step being approximately 10 mm, and a step-shaped inner wall with the rise of each step being approximately 4 mm and the run of each step being approximately 3 mm. A solid internally tapered cube portion 21 is disposed within the pyramid-shaped portion 19. The portion 21 is characterized by a rectangular shape in transverse cross-section through the isocenter 33, with a length of 20 mm and a width of approximately 10 mm. Each of the components is preferably made of acrylic such that a plurality of air-to-acrylic interfaces are visible on CT images. Other appropriate plastics having near-TEM (Tissue Equivalent Material) properties, such as polystyrene, may be used. In addition, the component 11 may be fabricated from tissue equivalent materials or may include oil (in place of air) with magnetic resonance properties.

Portion 21 has a tiny metal ball (not shown) embedded at the isocenter 33 of the phantom 9, and base 15 has a metal Z-line wire embedded therein. The metal components shown in the CT images as high contrast points, which are used as reference markers during calibration.

The base 15 has adjustable leveling feet 23 and a level indicator 25 to ensure the phantom 9 is properly leveled prior to use.

Figure 4:
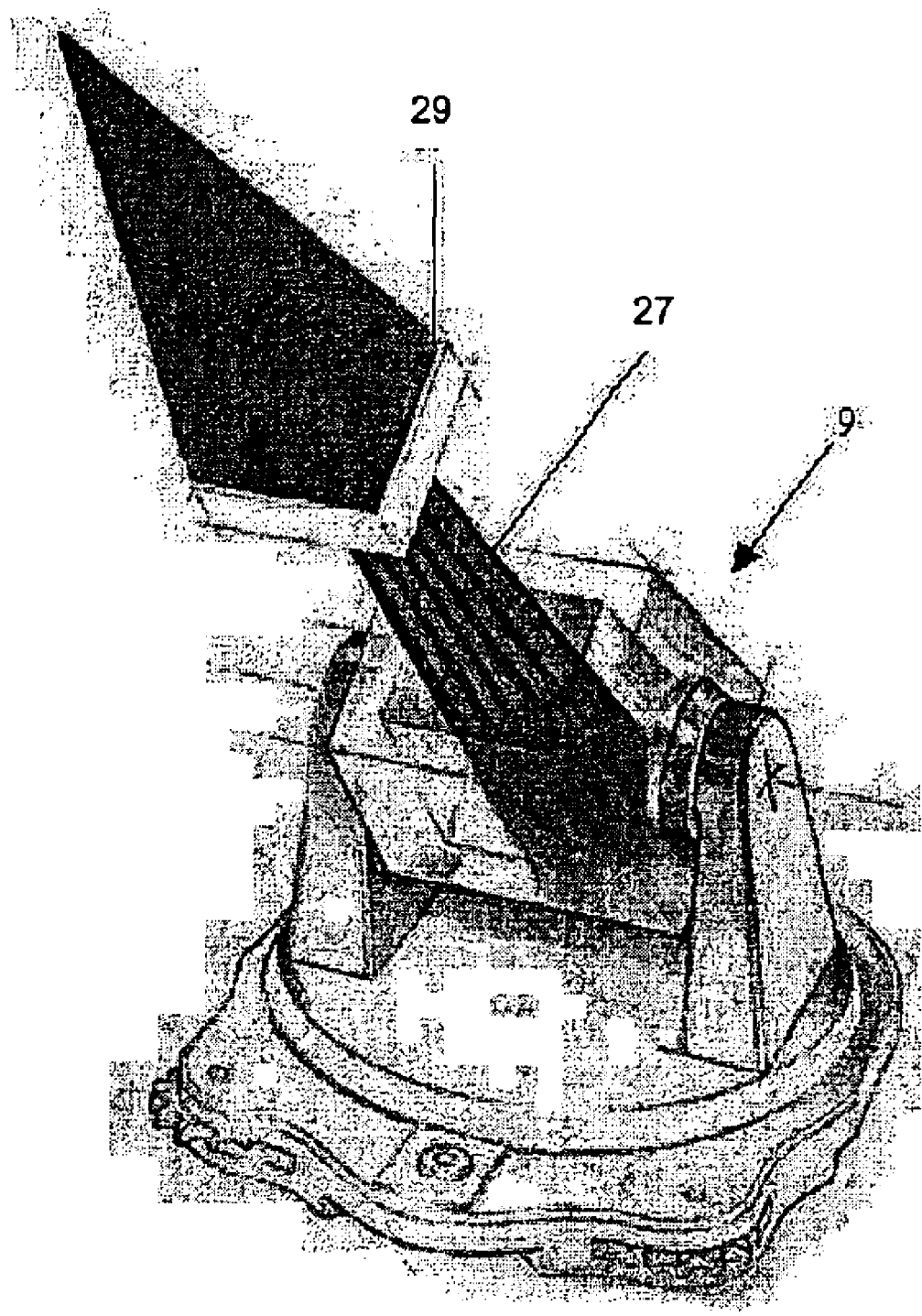
FIG. 4 is a schematic representation of the phantom of the present invention being irradiated by a conformal beam shaped by a multi-leaf collimator.

Turning to the schematic representation of FIG. 4, the phantom 9 is shown being irradiated by a beam 27 that has been shaped by a multi-leaf collimator 29. Because the geometry of the phantom 9 is known, the fidelity of the images obtained from radiation treatment device 1 can be assessed. The beam 27 is directed at the isocenter 33 of the rotatable component 11, with gantry and couch rotations corresponding to the orientation of the rotatable component 11 when it is scanned. The divergence of the air-to-acrylic phantom surfaces aligns with the 100 cm source axis distance of a conventional linear accelerator. By comparing the images of the irradiated phantom 9 against the known phantom geometry, information on image distortions, orientation, image slice and thickness are easily obtained. For proper QA, the beam display should agree with the phantom geometry in all available views, including transverse slices, multiplanar image reconstructions, DRRs, etc.

In operation, to assess QA of the radiation treatment installation, the following general steps are executed: (a) set the desired phantom rotations; (b) acquire a CT data set for the phantom; (c) transfer the CT data to the planning software; and (d) compare the beam or anatomy display/data measured by the planning software with the known values for the phantom 9 (e.g. geometry, volumes, electron densities).

Figure 5A:
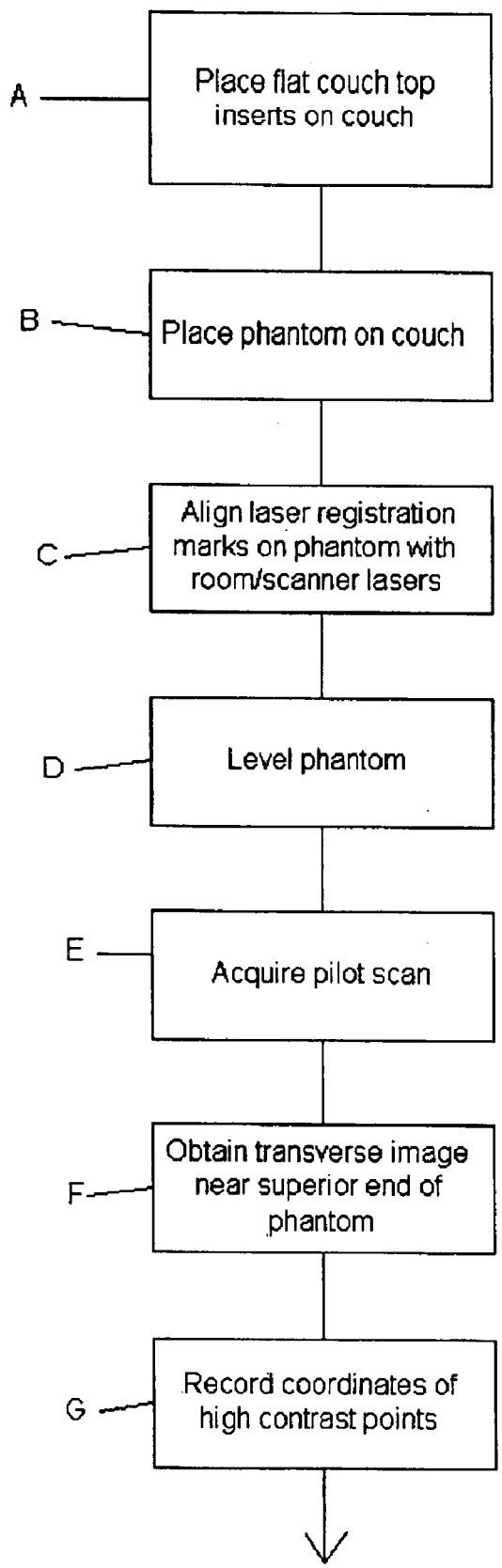
FIG. 5 is a flowchart showing the steps involved in acquiring a CT data set.
Figure 5B:
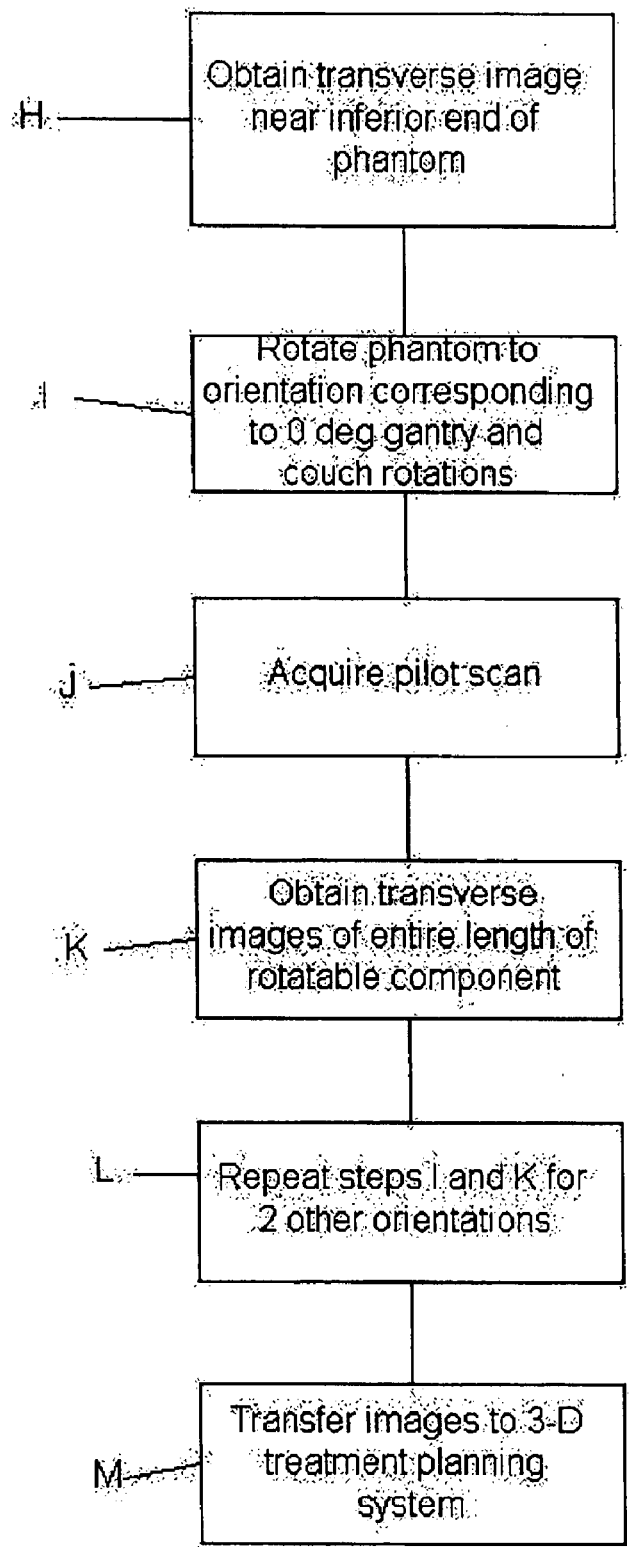

More particularly, the first step in assessing QA of the device 1 is to acquire a CT data set. This requires precise positioning of the phantom 9 on the CT scanner couch 7, and acquiring scans with the phantom rotated to correspond to the desired beam orientations. As shown in the flow chart of FIG. 5, flat couch top inserts are first placed on the CT scanner couch 7 (step A). Next, according to step B, the phantom 9 is then placed on the couch 7, with the rounded end of the base 15 closest to the CT gantry 5. In step C, lasers or CT scanner lasers (not shown) are then used to align with the laser alignment marks 31 on the phantom 9. The phantom 9 is then leveled (step D), using the leveling feet 23 in the base 15. At step E, a pilot scan for use in locating the phantom in the subsequently acquired CT image set is acquired. A transverse image is then obtained near the superior end of the phantom 9 (step F). Using the CT scanner cursor function, the coordinates of the two outer Z-wire points 35 are recorded on the left and the right side of the base 15 (step G). A transverse CT image is next acquired near the inferior end of the phantom 9 and the coordinates of these points are also recorded (step H). The horizontal and vertical coordinates should agree within ±1 mm (high contrast points are shown in the CT scan of FIG. 6 embedded in base 15). If the coordinates do not agree, the position of the phantom 9 is adjusted and steps C—H are repeated. At step 1, the rotatable component 11 is rotated to the orientation corresponding to a gantry rotation of 0 degrees on a couch rotation of 0 degrees, and a pilot scan is acquired for the entire length of the phantom (step J). At step K, transverse CT images are acquired for the entire length of the rotatable component 11. For best results, it is recommended that slice thickness and spacing do not exceed 3 mm. Steps I through K are then repeated for two other rotatable component orientations. At least one other scan set should be performed with either the gantry 5 or couch 7 rotated to a multiple of 90 degrees, and one scan set at an oblique angle with neither the gantry nor couch rotated to a multiple of 90 degrees. Finally, at step M, the images are transferred to the 3-D radiation treatment planning system and/or CT simulator work station.

Registration of the treatment planning coordinate system with the coordinate system of the phantom 9 is an important process. This is necessary because the image slice thickness and spacing is generally much greater than the pixel size in transverse CT images. There are two methods for performing coordinate system registration. The first is most appropriate when the CT slices are relatively thick compared to the transverse CT pixel size. This method involves measuring the high contrast points in the base and fitting a straight line to find the coordinate of isocenter 33 along the scanning axis. The second method is most appropriate when the CT slice thickness is relatively small, the treatment planning software does not allow for easy measurements of the required data, or if software to perform a linear regression is not available.

Figure 6:
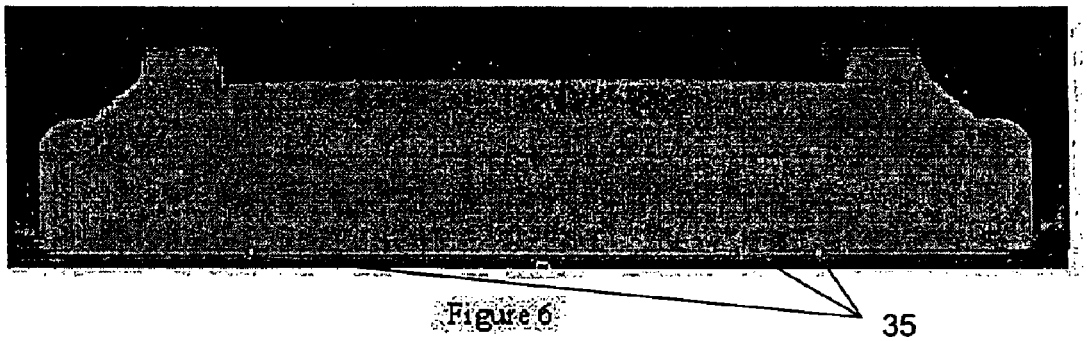
FIG. 6 is a scan showing a Z-line wire embedded in the base, used during acquisition of the CT data set.
Figure 7:
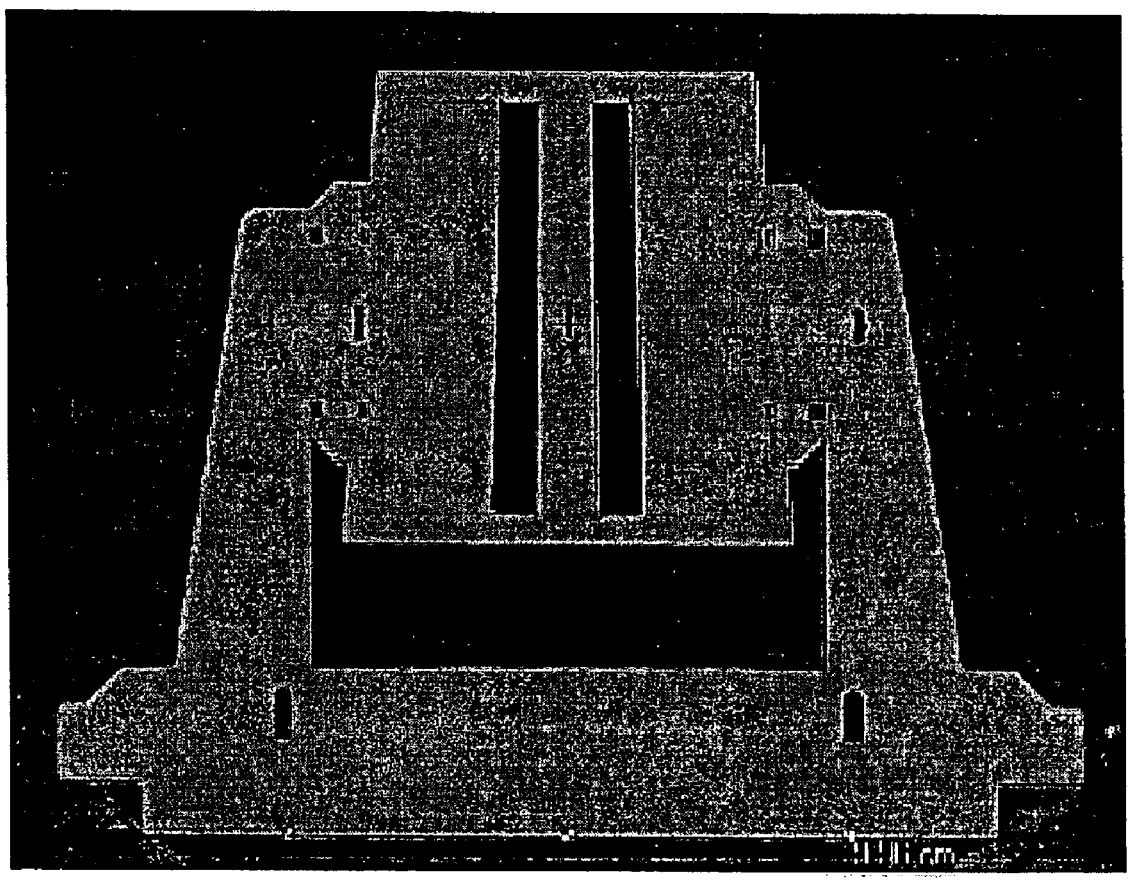
FIG. 7 shows use of a ruler function of the planning software to measure the distance between one of the outer wires of the Z-line wire and the central wire thereof.

According to the first coordinate system registration method, the technician initially determines the slice that is closest to the centre of the Z-line marker 35 on the base of the phantom (FIG. 6). This is the slice where the distance from either side wire to the central wire is 10 cm. Using the ruler function of the software (FIG. 7) the distance from one of the outer wires to the central wire is measured, and the couch index of the central wire is recorded. This measurement is repeated for four slices superior and four slices inferior to the central slice. Next, a linear regression fit of the couch index is performed versus the distance between the wires. Using the fit equation, the axial coordinate of the phantom's origin is determined (where the distance between the wires is 10 cm Finally, the horizontal origin coordinate is determined by calculating the mid-point of the horizontal coordinates of the left and right wires of the Z-line. The origin for the vertical axis is at the height of the metal ball 33 in the centre of the phantom 9 (the position of the metal ball at isocenter 33 is indicated in FIG. 3, though because of its small size, the ball itself is not visible in the figure).

According to the second method which, as discussed above, may be more appropriate when software tools for determining the coordinates are insufficient, the technician scans through the transverse CT images and finds the slice or slices where the high contrast point corresponding to the metal ball at isocenter 33 appears. The origin can be assumed to be the position of the high contrast point. If the high contrast point appears on multiple images, then the coordinate along the axis of scanning must be approximated as well as possible.

Image acquisition and transfer tests are designed to quickly assess a few aspects of the CT images to ensure that they have been correctly acquired by the scanner and correctly transferred to the treatment planning software. Failure of any of these tests may indicate errors in image acquisition and transfer. First, the technician verifies that the central and right Z-line wires intersect at the inferior end of the Z-line to confirm the orientation of the image set. A Z-line regression may then be formed to ensure that the scope of the regression equation is 1.00 ±0.05. Deviation from this may indicate either poor measurement of the Z-line geometry or an error in the image slice thickness and/or spacing.

Figure 8A:
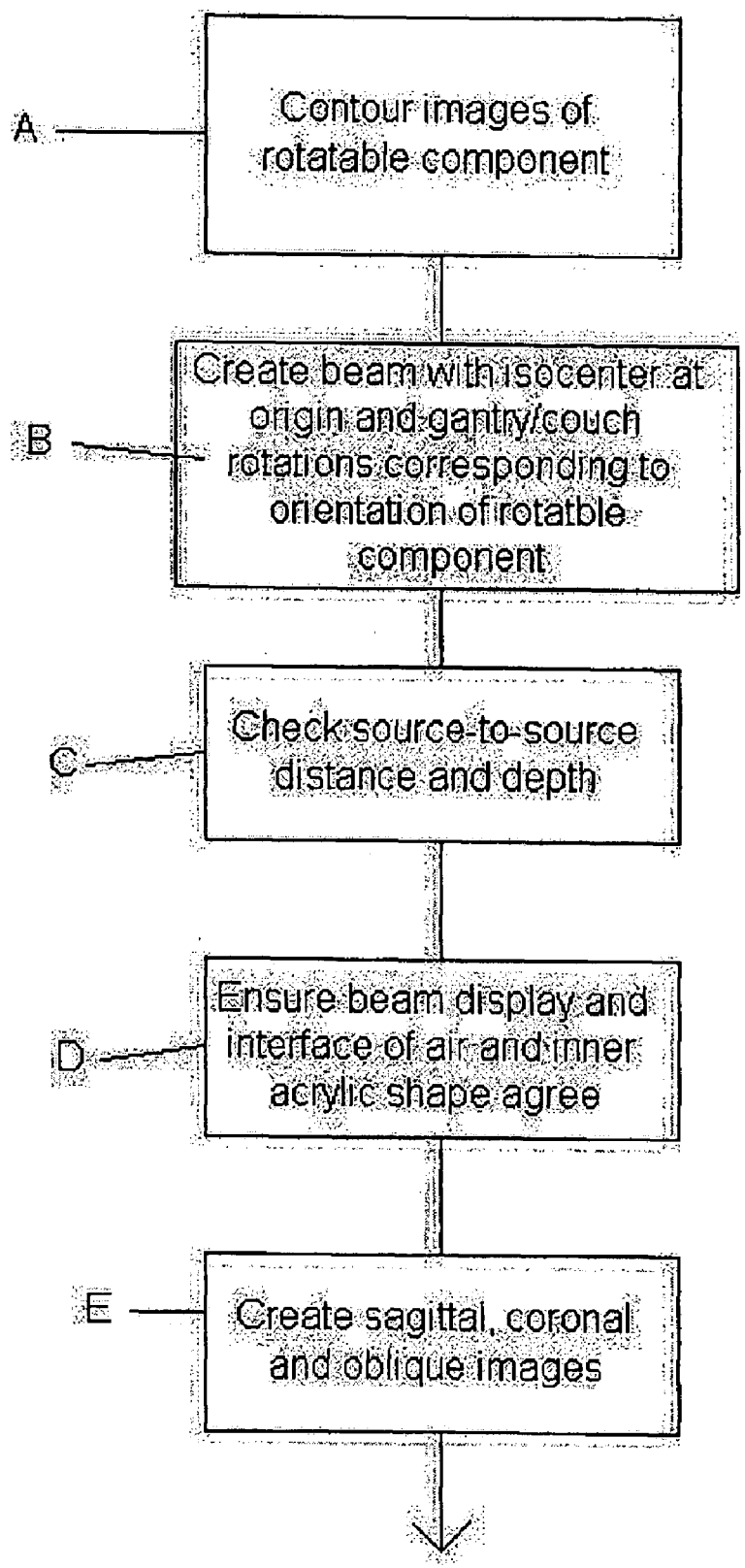
FIG. 8 is a flowchart showing the steps involved in conducting a beam display test.
Figure 8B:
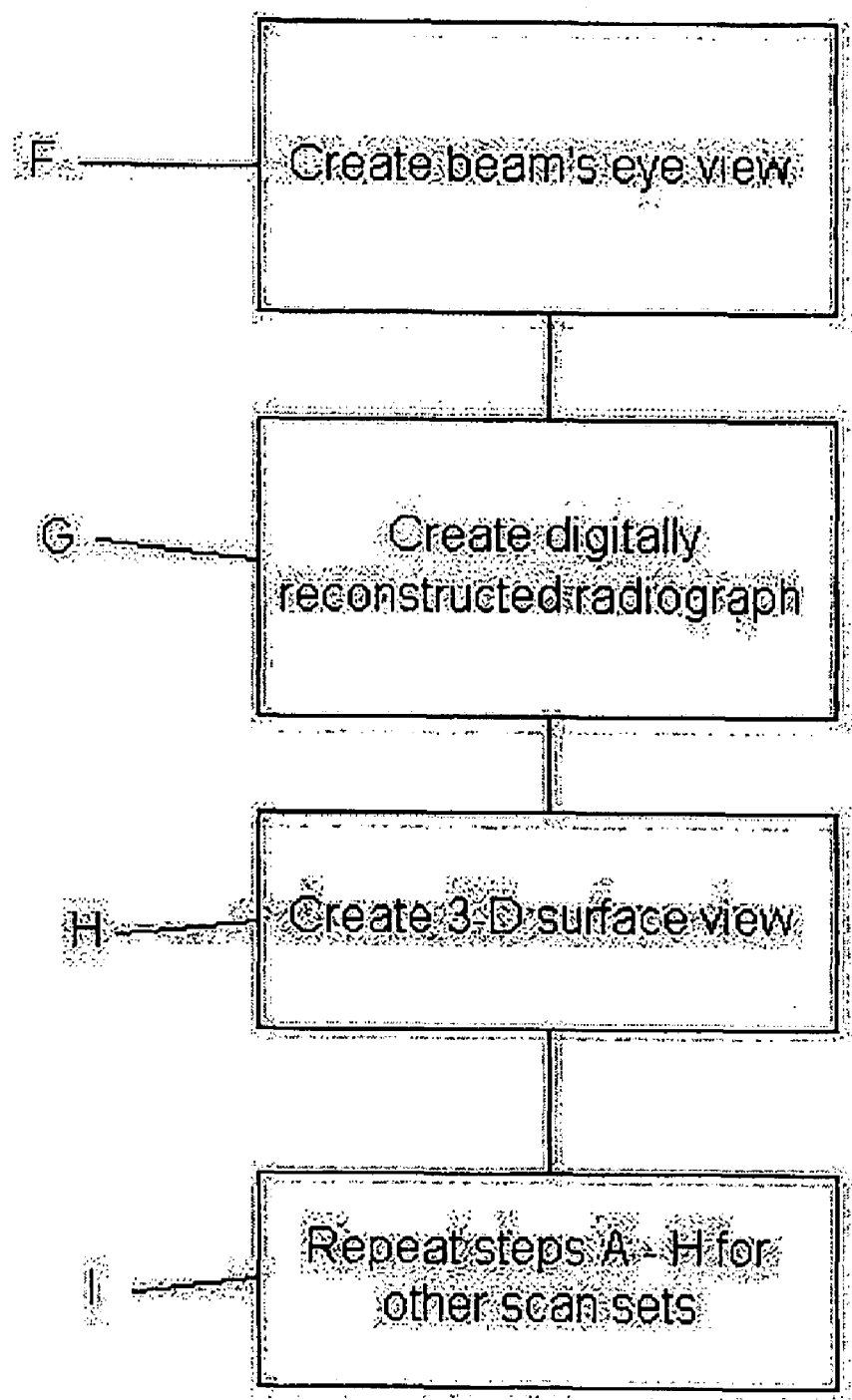
Figure 9A:
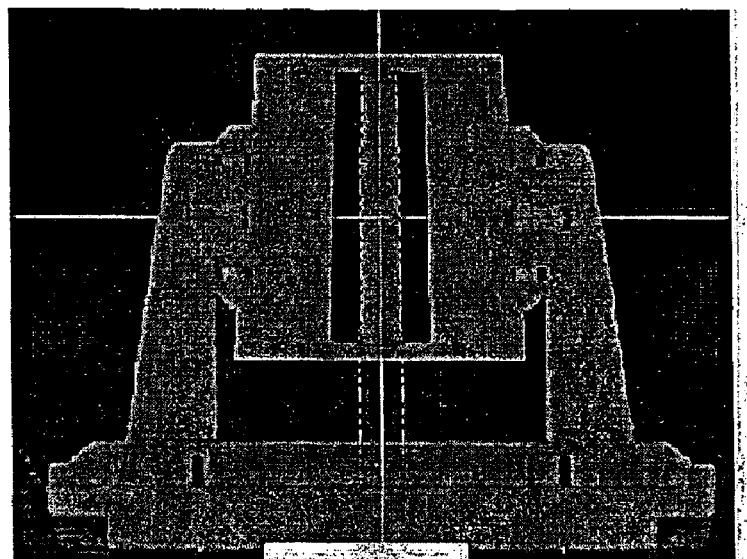
FIG. 9 shows a radiation field superimposed on the phantom of the present invention, for a gantry rotation of 0 degrees and couch rotation of 90 degrees (FIG. 9A), and a gantry rotation of 323 degrees and couch rotation of 204 degrees (FIG. 9B)
Figure 9B:
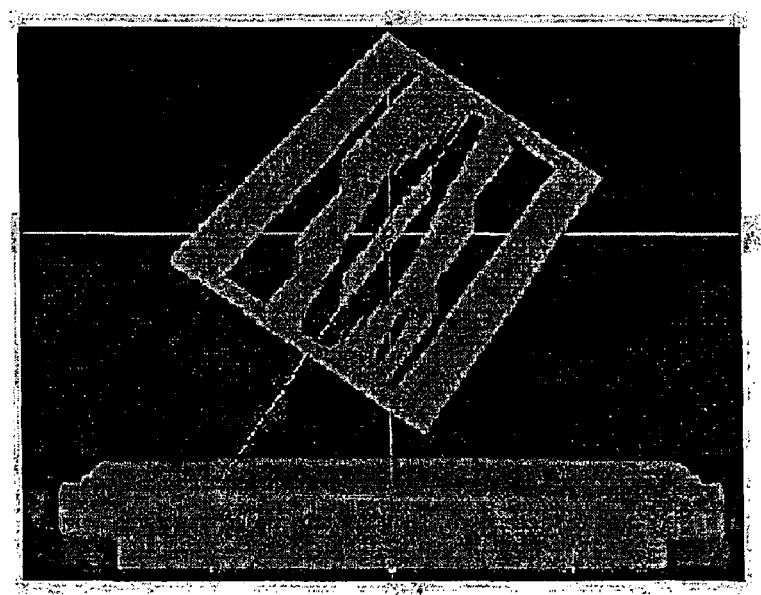
Figure 10A:
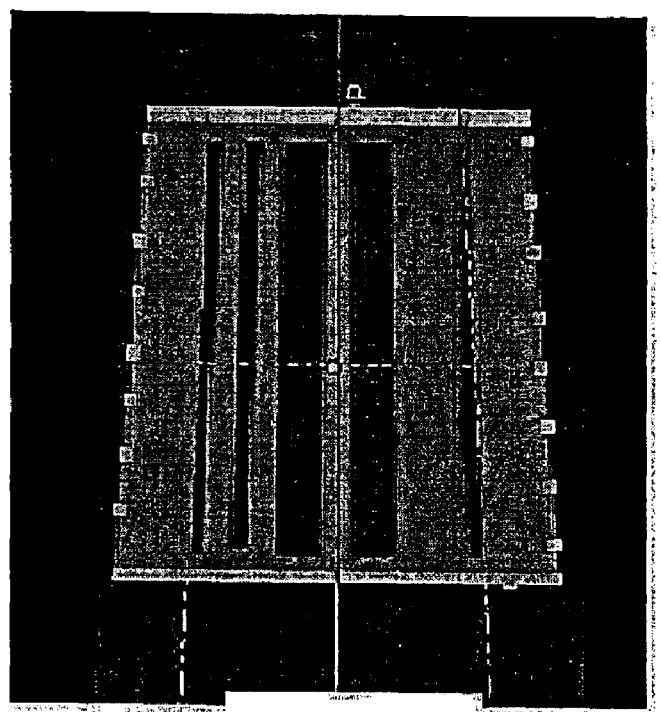
FIG. 10 shows a radiation field superimposed in the sagittal reconstructed image of the phantom for a gantry rotation of 0 degrees and a couch rotation of 90 degrees (FIG. 10A), and a gantry rotation of 323 degrees and a couch rotation of 204 degrees (FIG. 10B)
Figure 10B:
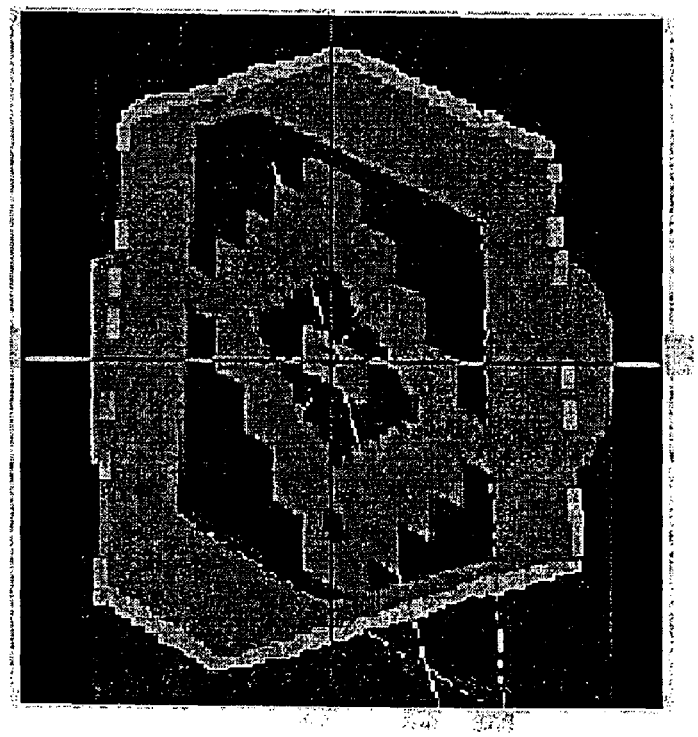
Figure 11A:
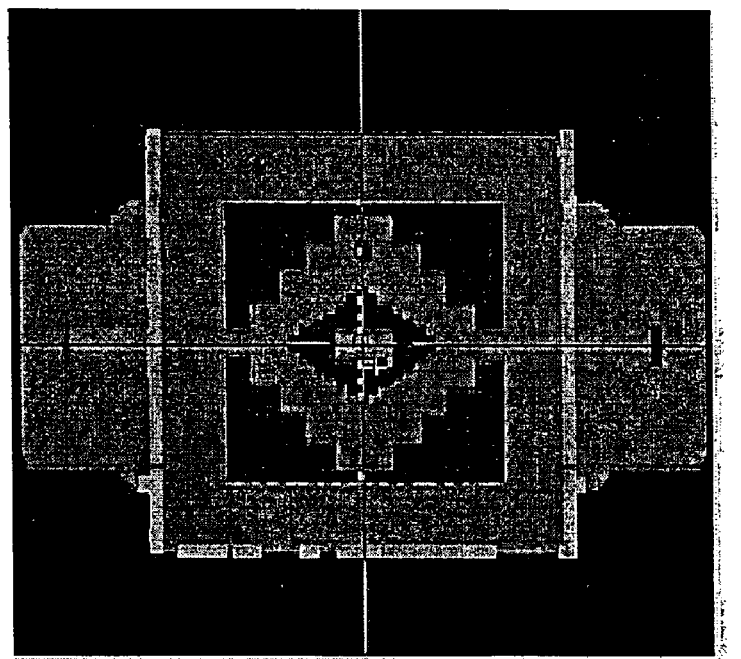
FIG. 11 show a radiation field superimposed on a coronal reconstructed image of the phantom for a gantry rotation of 0 degrees and a couch rotation of 90 degrees (FIG. 11A), and a gantry rotation of 323 degrees and a couch rotation of 204 degrees (FIG. 11B)
Figure 11B:
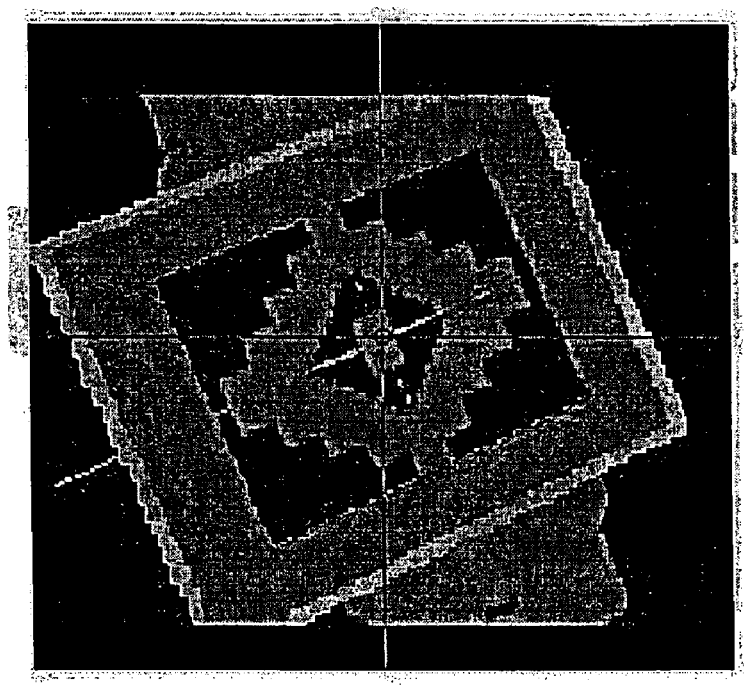
Figure 12A:
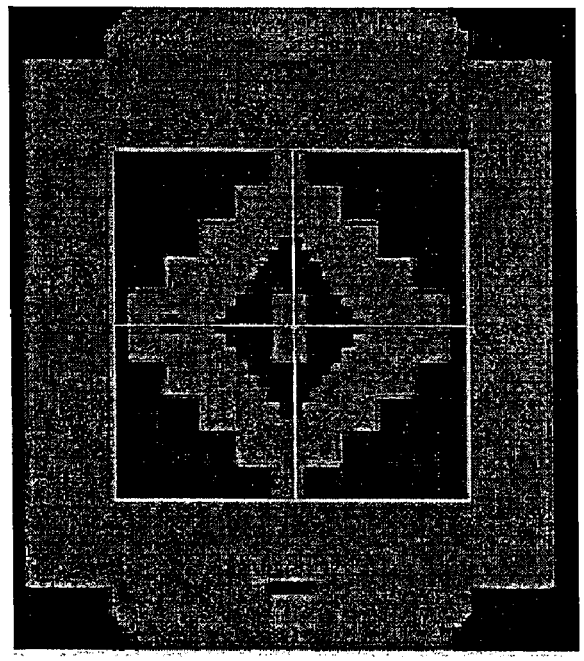
FIG. 12 shows a radiation field superimposed on an oblique reconstructed CT image of the phantom for a gantry rotation of 0 degrees and a couch rotation of 90 degrees (FIG. 12A), and a gantry rotation of 323 degrees and a couch rotation of 204 degrees (FIG. 12B)
Figure 12B:
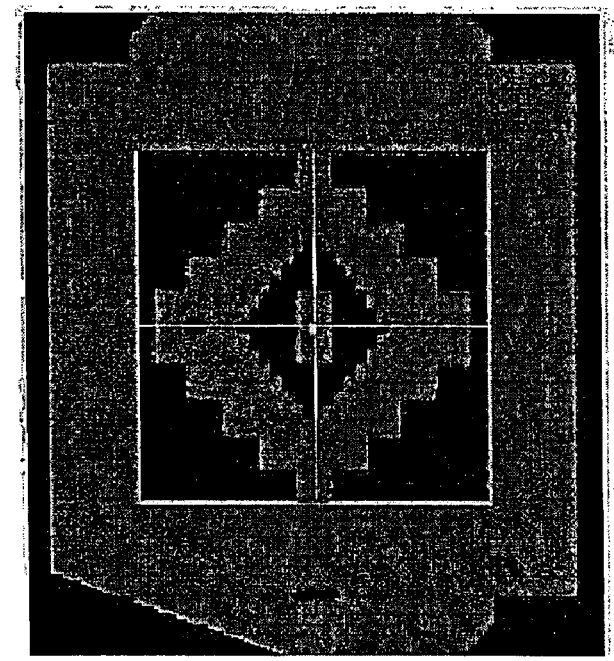
Figure 13A:
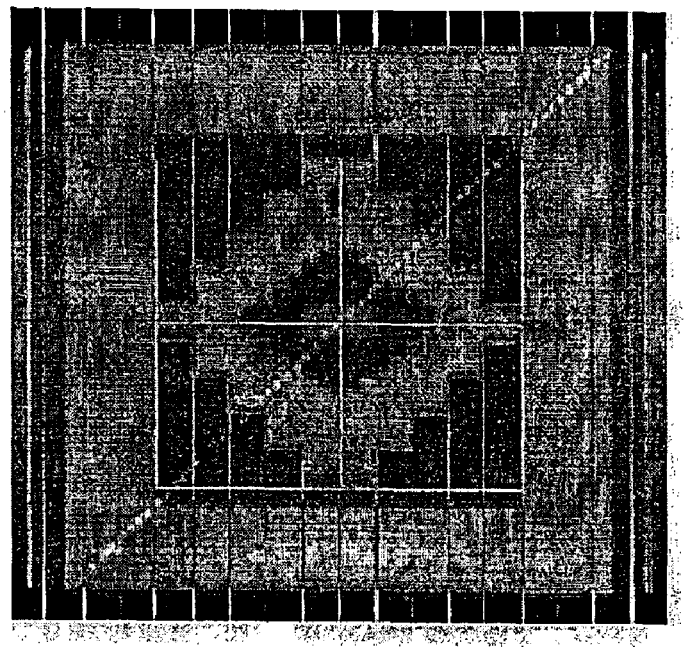
FIG. 13 shows an MLC shaped radiation field superimposed on a digitally reconstructed radiograph of the phantom for a gantry rotation of 0 degrees and a couch rotation of 90 degrees (FIG. 13A), and a gantry rotation of 323 degrees and a couch rotation of 204 degrees (FIG. 13B)
Figure 13B:
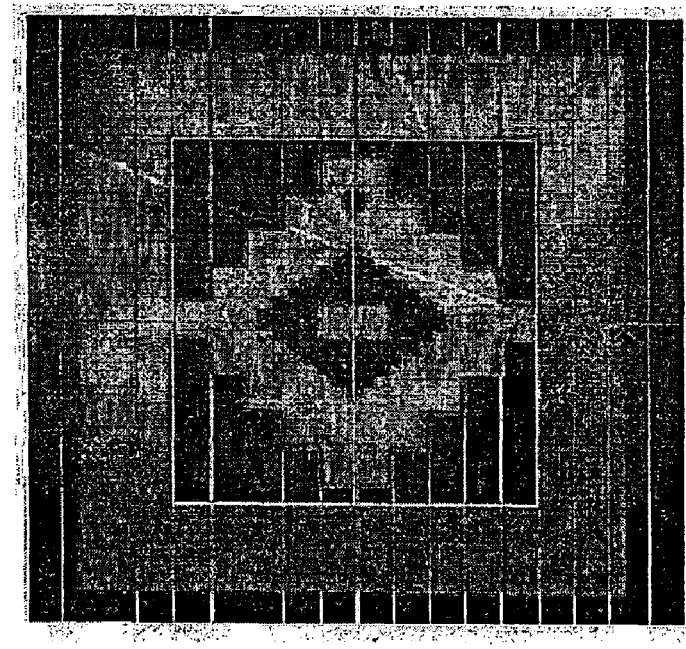

Beam display tests may also be conducted to permit assessment of the display of radiation beam geometry in the treatment planning software. These allow the testing of multiple field apertures on transverse, sagittal, coronal, and oblique CT images, beam's eye views, digitally reconstructed radiographs (DRRs), and 3-D views for any combination of gantry and couch rotations. FIG. 8 is a flow chart showing the steps for conducting a beam display test. At step A, the CT images of the rotatable component 11 are contoured, identifying the edges of all tapered surfaces. Since the contours may obscure the phantom geometry in some views, step A may be performed later. At step B, a beam is created with its isocenter at the isocenter 33 of the rotatable component 11, with a 10×10 $cm^2$ field size, and with gantry and couch rotations corresponding to the orientation of the rotatable component. At step C, the source-to-surface distance and depth are checked for correctness. As indicated above, the phantom geometry is correct for a 100 cm source-to-axis geometry, according to the preferred embodiment. At step D, the technician ensures that the graphical beam display and the interface of the air and inner acrylic shape 21 agree to within ±2 mm on transverse CT images. Step D is repeated for 1×2 $cm^2$, and 15×15 $cm^2$ field sizes, as well as different MLC leaf arrangements. FIG. 9 shows a 2×1 $cm^2$ radiation field superimposed on the phantom for a gantry rotation of 0 degrees and couch rotation of 90 degrees (FIG. 9A), and a gantry rotation of 323 degrees and couch rotation of 204 degrees (FIG. 9B). The beam edges align with the outer dimensions of the inner acrylic shape 21, indicating that the beam is displayed correctly. At step E, sagittal, coronal, and (if possible) oblique reconstructed CT images are created. The technician should ensure that the beam graphics and phantom geometry agreed to within ±3 mm for all field sizes. This accuracy may vary with slice thickness and spacing, wherein very coarse slices exhibit worse agreement, while very fine slices exhibit better agreement. FIG. 10 shows a 10×10 cm² radiation field superimposed on a sagittal reconstructed CT image for a gantry rotation of 0 degrees and a couch rotation of 90 degrees (FIG. 10A), and a gantry rotation of 323 degrees and a couch rotation of 204 degrees (FIG. 10B). The beam edges align with the outer dimensions of the air cavity adjacent the inner wall of cubic element 17, indicating that the beam is correctly displayed. FIG. 11 shows a 10×10 cm² radiation field superimposed on a coronal reconstructed CT image for a gantry rotation of 0 degrees and a couch rotation of 90 degrees (FIG. 11A), and a gantry rotation of 323 degrees and a couch rotation of 204 degrees (FIG. 11B). The beam edges align with the outer dimensions of the air cavity adjacent the inner wall of cubic component 17, indicating that the beam is correctly displayed. FIG. 12 shows a 10×10 cm² radiation field superimposed on an oblique (normal to the central beam axis) reconstructed CT image for a gantry rotation of 0 degrees and a couch rotation of 90 degrees (FIG. 12A), and a gantry rotation of 323 degrees and a couch rotation of 204 degrees (FIG. 12B). The beam edges align with the outer dimensions of the air cavity adjacent the inner wall of component 17, indicating that the beam is correctly displayed. At step F, a beam's eye view is created to ensure that the field sizes correspond to the contoured materials within ±4 mm. At step G, a digitally reconstructed radiograph is created (FIG. 13) to ensure that the field sizes correspond to the phantom geometry within ±3 mm. Specifically, FIG. 13 shows an MLC shaped radiation field superimposed on a digitally reconstructed radiograph for a gantry rotation of 0 degrees and a couch rotation of 90 degrees (FIG. 13A), and a gantry rotation of 323 degrees and a couch rotation of 204 degrees (FIG. 13B). The beam edges align with the dimensions of the inner acrylic shape 19, indicating that the beam is displayed correctly. At step H, a 3D surface view is created of the rotatable component geometry to ensure that the beam geometry agrees within ±4 mm for all available 3D views. Finally, at step 1, steps A-H are repeated for the remaining scan sets.

Figure 14:
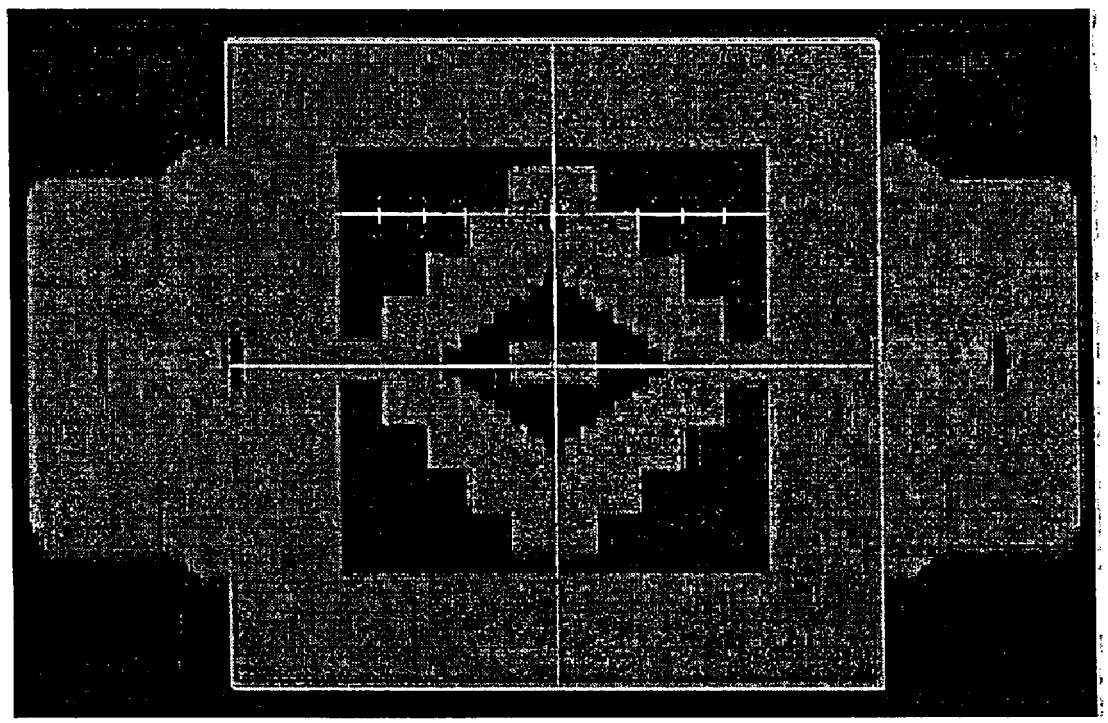
FIG. 14 shows a reconstructed coronal CT image through the centre of the phantom according to the present inventions.

Multiplanar CT image reconstruction tests may be used to assess the accuracy of the anatomy displayed on multiplanar CT image reconstructions (i.e. to test general image quality and geometric accuracy). The software ruler function is used to measure the dimensions of the shapes. Firstly, a sagittal CT image is constructed. Next, for east of the materials, the technician ensure that the geometry displayed is consistent with the known phantom geometry within ±4 mm (this limit depends on the scan parameters) by measuring the imaged dimensions of the components 17, 19 and 21 using the software ruler function. The inner acrylic rectangle 21 should measure 1×2 cm², the air square adjacent inner wall of component 17 should measure 10×10 cm², and the outer wall of acrylic square 17 should measure 15×15 cm². These steps are repeated for a coronal CT image (FIG. 14), and an oblique image, if possible. The multiplanar CT image reconstructions are then repeated for all CT scan sets.

Figure 15:
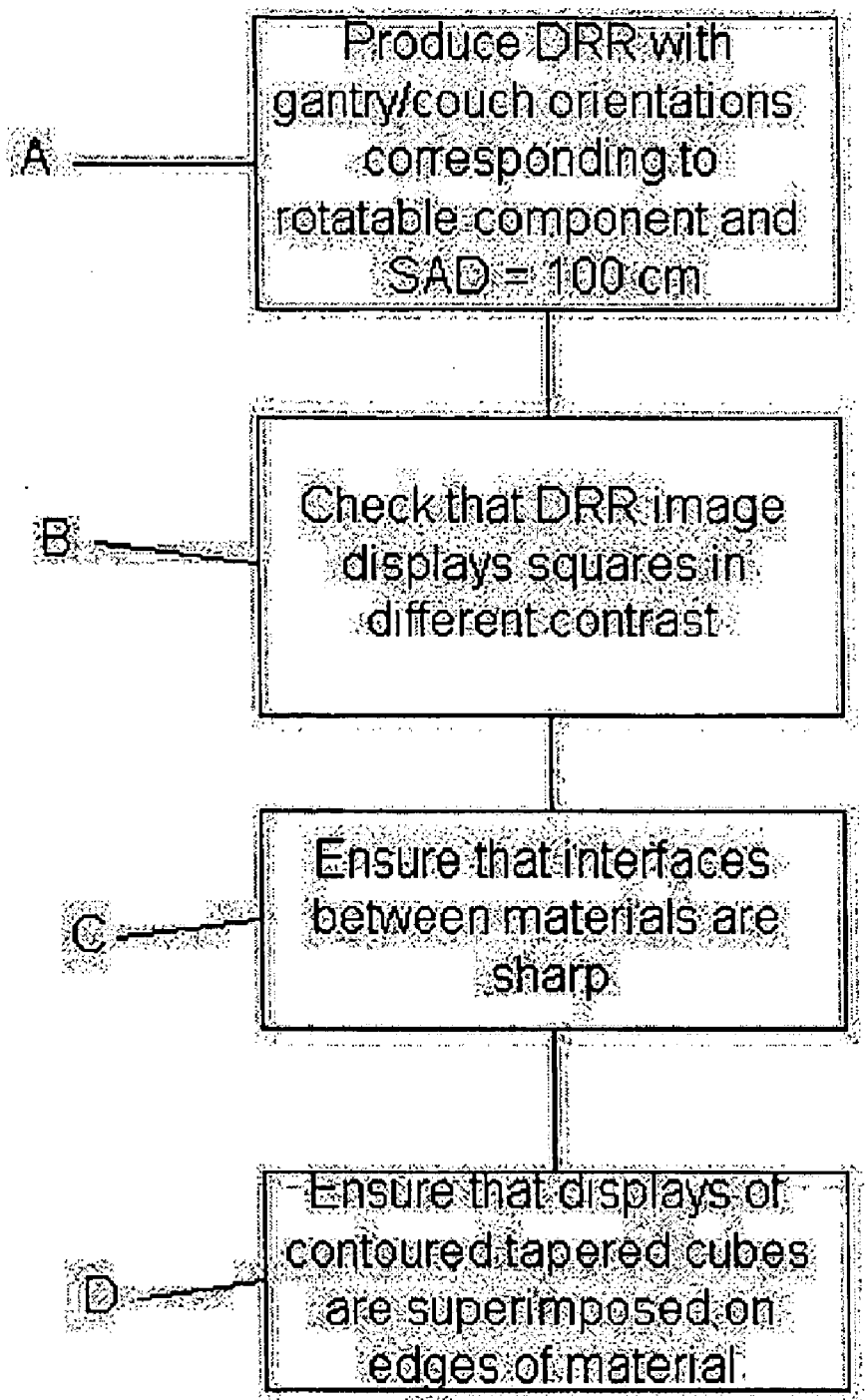
FIG. 15 is a flow chart showing the steps involved in conducting a test for the geometric accuracy of digitally reconstructed radiograph (DRR) images.
Figure 16:
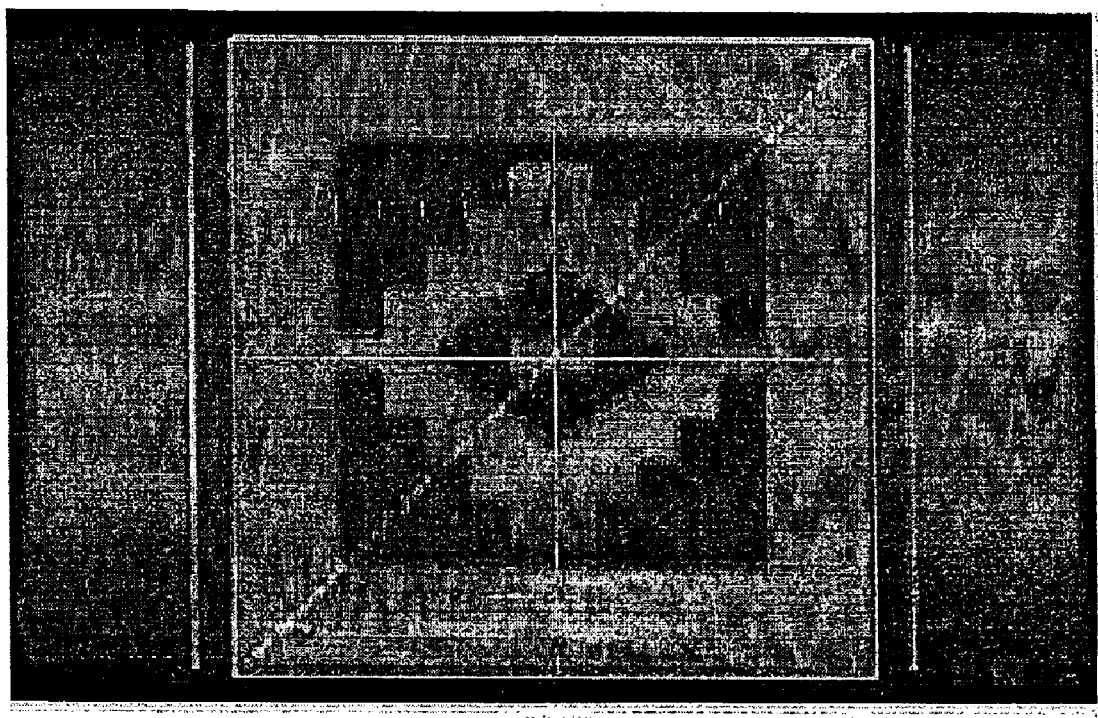
FIG. 16 shows a digitally reconstructed radiograph of the phantom according to the present invention.

Tests may also be performed to check the geometric accuracy of digitally reconstructed radiograph (DRR) images, as well as contoured anatomy superimposed on the images. At step A of FIG. 15, a DRR is produced with gantry and couch orientations that correspond to the orientation of the rotatable component 11, and a source axis distance of 100 cm. At step B, the technician checks that the DRR image displays three squares of different contrast and ensures that the height and width of each square corresponds to the phantom geometry (i.e. the size that the isocentre multiplied by any magnification factor). At the isocentre, the inner acrylic rectangle 17 is 1×2 cm², the air square is 10×10 cm², and the outer wall of acrylic square 17 is 15×15 cm². At step C, the technician ensures that the interfaces between the materials are sharp and not significantly blurred, and that the penumbra between materials is no larger than 4 mm. Blurring can indicate errors in the ray line divergence of the DRR. Finally, at step D, the technician ensures that the displays of any contoured tapered cubes are superimposed on the edge of the appropriate material. FIG. 16 shows a digitally reconstructed radiograph of the phantom 9. The software ruler function is used to measure the dimensions of the shapes. As seen in FIG. 16, the outer dimensions of the air cavity measure 10 cm across, indicating that it is correctly displayed.

Figure 17:
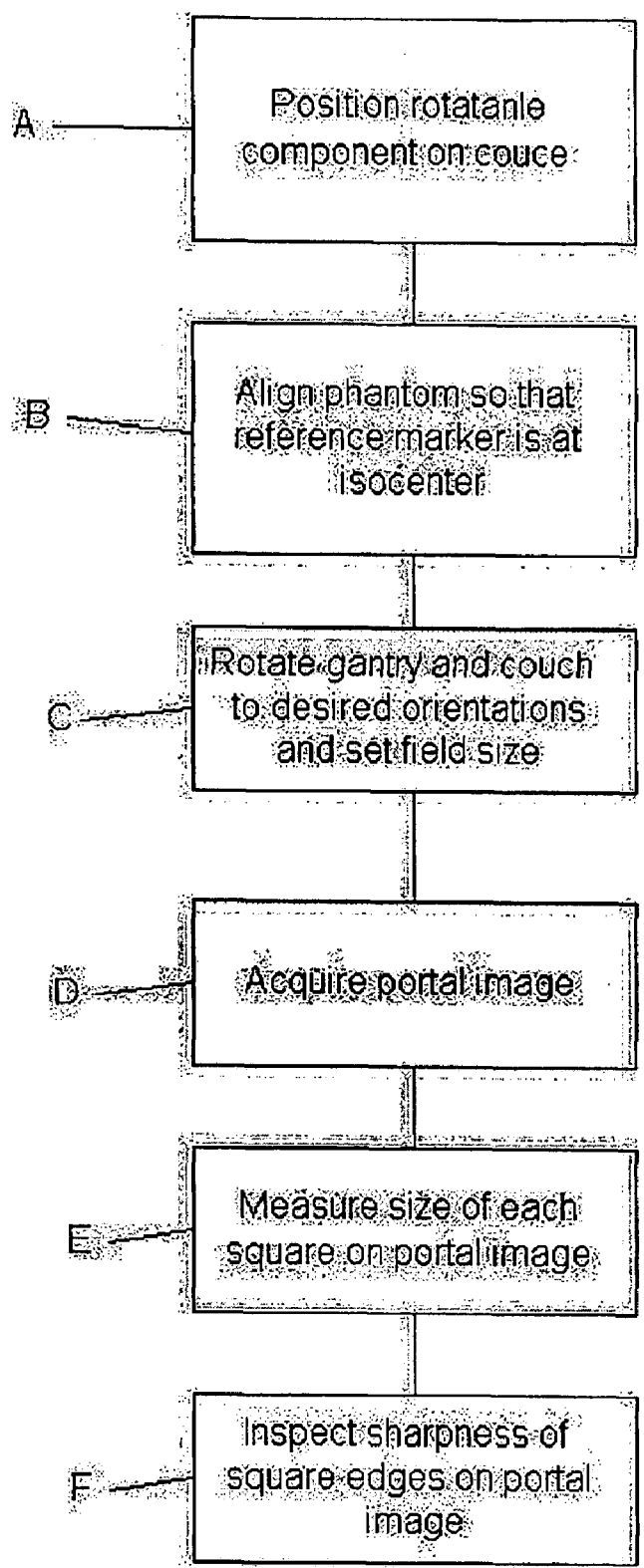
FIG. 17 is a flowchart showing the steps involved in conducting a test for verifying the geometry in film or electronic portal imaging.

In addition to the QA of radiation treatment planning software as set forth in detail above, the phantom 9 according to the present invention can also be used to implement a QA program for film or electronic portal imaging in order to verify the imaging geometry for any combination of gantry and couch angles. The steps for performing portal imaging tests are set forth in FIG. 17. At step A, the technician positions the rotatable component 11 on the linear accelerator couch 7. Using the treatment room lasers and the linear accelerator light field (not shown), the phantom 9 is aligned (step B) such that the reference marker in the centre of the rotatable component is at the isocenter 33. At step C, the gantry and couch are rotated to the desired orientations and the field size is set to 15×15 cm². At step D, the portal image is acquired. The size of each square is measured on the portal image (step E), wherein each square should be the size defined at the isocenter 33, multiplied by the portal image magnification. At the isocentre 33, the inner acrylic rectangle 21 is 1×2 cm², the air square is 10×10 cm², and the outer wall of acrylic square 17 is 15×15 cm². Finally, at step F, the sharpness of the square edges are inspected on the image portal. These edges should appear sharp. Blurred edges may indicate misalignment of the gantry and the imager. An intensity profile through the image may be conducted to determine this more quantitatively, if available.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the purpose and scope of the invention.

What is claimed is:

1. A phantom for evaluating nondosimetric functions in radiation therapy installation having a patient couch and a gantry with a head thereon for generating a multi-leaf collimated beam, wherein the beam is directed toward said couch at an orientation dictated by relative orientations of said couch and gantry, comprising:

a base adapted for disposition on said couch; and a component mounted to said base for rotation in accordance with said relative orientations of the couch and gantry, said component incorporating a plurality of known geometrical structures corresponding in shape to said multi-leaf collimated beam whereby upon irradiating said component with said beam to obtain an image thereof said nondosimetric functions may be evaluated by comparing the image of said component with said known geometrical structures and identifying discrepancies therebetween.

2. The phantom of claim 1, wherein said base further includes a levelling mechanism.

3. The phantom of claim 1, wherein said base further includes a level indicator.

4. The phantom of claim 1, wherein said plurality of known geometrical structures includes a tapered cube-shaped component.

5. The phantom of claim 4, wherein said plurality of known geometrical structures includes pyramid-shaped component disposed within said cube-shaped component.

6. The phantom of claim 5, wherein said plurality of known geometrical structures includes a further tapered cube-shaped component disposed within said pyramid-shaped component 7. The phantom of claim 6, wherein said further cube-shaped component includes a centrally disposed ball for aligning said phantom with the isocenter of said beam.

8. The phantom of claim 1, wherein said geometrical structures are fabricated from acrylic.

9. The phantom of claim 1, wherein said geometrical structures are fabricated from plastic with near-TEM properties.

10. The phantom of claim 1, wherein said geometrical structures are fabricated from tissue-equivalent material.

11. The phantom of claim 1, wherein said geometrical structures are fabricated from materials with magnetic resonance properties.

12. The phantom of claim 1, wherein air occupies space between each of said geometrical structures.

13. The phantom of claim 1, wherein oil occupies space between each of said geometrical structures.

14. The phantom of claim 1, wherein said base includes a z-wire to facilitate proper orientation of the phantom with said radiation treatment system.

15. The phantom of claim 1, wherein said base includes laser registration marks to facilitate proper orientation of the phantom with said radiation treatment system.

* * * * *